United States Patent [19]

Raspanti et al.

[11] Patent Number: 5,665,334
[45] Date of Patent: Sep. 9, 1997

[54] BENZOFURAN DERIVATIVES AND METHODS FOR THEIR USE AS STABILIZERS AND SUNSCREENS AGAINST HIV RADIATIONS

[75] Inventors: Giuseppe Raspanti; Giorgio Zanchi, both of Bergamo, Italy

[73] Assignee: 3V Inc., Weehawken, N.J.

[21] Appl. No.: 576,347

[22] Filed: Dec. 21, 1995

[51] Int. Cl.$^6$ .................... A61K 7/42; C07D 307/82
[52] U.S. Cl. .................... 424/59; 424/60; 106/287.2; 430/931; 514/469; 528/935; 546/196; 549/469
[58] Field of Search ............... 549/469; 424/59; 514/469

[56] References Cited

U.S. PATENT DOCUMENTS 5,362,481 11/1994 Raspanti et al. ................. 549/469

Primary Examiner—Bernard Dentz
Attorney, Agent, or Firm—Griffin, Butler Whisenhunt & Kurtossy

[57] ABSTRACT

Compounds of the general formula I

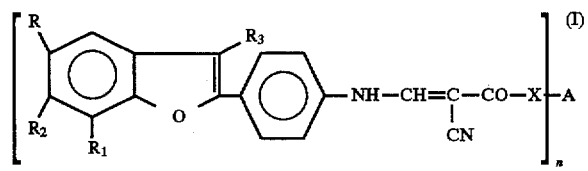

R and $R_1$, which can be the same or different, are hydrogen or a $C_1$–$C_8$ straight or branched alkyl group, $R_2$ is hydrogen or the group $OR_4$, wherein $R_4$ is a $C_1$–$C_4$ alkyl group, $R_3$ is hydrogen, methyl or ethyl, X is oxygen or the $NR_5$ group, wherein $R_5$ is hydrogen or $C_1$–$C_{18}$ straight or branched alkyl group n is the number 1 or 2, A, when n is 1, is a $C_1$–$C_{20}$ straight or branched alkyl group, $C_6$–$C_{12}$ cycloalkyl group, the group of formula (II),

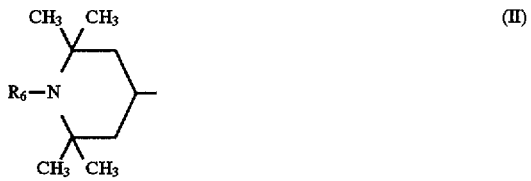

wherein $R_6$ is hydrogen or methyl group or a group of formula (III)

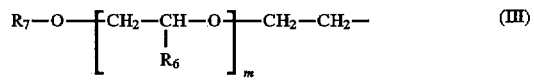

wherein $R_6$ has the above meanings and $R_7$ is $C_1$–$C_{18}$ straight or branched alkyl group, phenyl, optionally substituted with a $C_1$–$C_4$ straight or branched alkyl group, m can have the values from 0 to 4, A, when n is 2 is $C_2$–$C_{12}$ alkylene or the group of formula (IV)

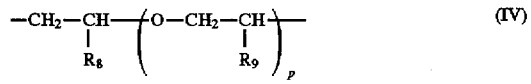

wherein $R_8$ and $R_9$, which may be the same or different, are hydrogen or methyl group, p is a number from 1 to 4, have stabilizing activity against UV radiation and are useful in cosmetics and plastic materials.

21 Claims, No Drawings

_5,665,334_

BENZOFURAN DERIVATIVES AND METHODS FOR THEIR USE AS STABILIZERS AND SUNSCREENS AGAINST HIV RADIATIONS

The present invention relates to compounds having high absorption towards ultraviolet radiation, therefore the compounds are useful as photostabilizers and sunscreens, particularly in cosmetics and plastics.

BACKGROUND OF THE INVENTION

Ultraviolet (UV) radiations of sunlight ranging from 280 to 400 nm are known to exert a damaging action on organic materials, such as plastics and paints, which are destroyed more or less rapidly. Destruction is apparent in the form of yellowing, discolouration, brittlening and generally as a loss of m (I) to said polymers. Another object of the present invention is a method for protecting human skin from noxious sunlight radiations by applying on the skin a cosmetic composition containing an effective amount of at least a compound of formula (I) as sunscreen. Another object of the present invention is a cosmetic composition containing an effective amount of at least one compound of formula (I) as active ingredient.

DETAILED DESCRIPTION OF THE INVENTION

According to the present invention, in the compounds of formula (I), examples of $C_1-C_4$, $C_1-C_8$, $C_1-C_{18}$, $C_1-C_{20}$, straight or branched alkyl group are: methyl, ethyl, propyl, isopropyl, butyl, isobutyl, tertbutyl, pentyl, neopentyl, hexyl, 2-, 3- or 4-methylpentyl, 2 ethylhexyl, heptyl, 1-ethylpentyl, 4-methylhexyl, octyl, nonyl, 5-ethylheptyl, 6-methyloctyl, decyl, tetradecyl, 3-methyl-5-propyl-7-ethyldecyl, octadecyl.

Examples of $C_6-C_{12}$ cycloalkyl group are: cyclohexyl, cycloheptyl, methylcyclopentyl, tert-butylcyclohexyl, methylcyclopentyl, cyclooctyl, cyclododecyl.

Examples of $C_1-C_4$ alkoxy group are: methoxy, ethoxy, isopropoxy, tertbutoxy.

Examples of optionally substituted phenyl group are: o-, m-, or p-toluyl, o-, or p-xylyl, o-, m-, or p-ethylphenyl, o-, m-, or p-tertbutylphenyl or phenyl groups bearing one or more same or different alkyl groups.

Examples of $C_2-C_{12}$ alkylene group are: ethylene trimethylene, pentamethylene, heptamethylene, decamethylene, dodecamethylene.

A first class of preferred compounds of formula (I) are those wherein X is oxygen.

A second class of preferred compounds of formula (I) are those wherein X is oxygen, R and $R_1$, which can be the same or different, are hydrogen or a $C_1-C_8$ straight or branched alkyl group, $R_2$ is hydrogen.

Particularly preferred compounds are those of formula (I) wherein the groups are as defined in the following Table 1:

TABLE 1

| | R | $R_1$ | $R_2$ | $R_3$ | X | n | A |
|---|---|---|---|---|---|---|---|
| 1 | H | H | H | H | O | 1 | $C_2H_5$ |
| 2 | H | H | H | H | O | 1 | $CH_2CH-C_4H_9$ <br> $\|$ <br> $C_2H_5$ |
| 3 | H | H | H | $CH_3$ | O | 1 | $C_2H_5$ |
| 4 | H | H | H | H | O | 1 | $C_{10}H_{21}$ |
| 5 | H | H | H | H | O | 1 | $CH_3-N\diagup\diagdown$ |
| 6 | H | H | H | H | O | 1 | $(CH_2)_2O(CH_2)_2OCH_3$ |
| 7 | H | H | H | H | O | 1 | $(CH_2)_2O(CH_2)_2OC_4H_9$ |
| 8 | H | H | H | H | O | 1 | $C_{12}H_{25}$ |
| 9 | H | H | H | $CH_3$ | O | 1 | $CH_2-CH-C_4H_9$ <br> $\|$ <br> $C_2H_5$ |
| 10 | H | H | H | $CH_3$ | O | 2 | $(CH_2)_{10}$ |
| 11 | H | H | H | H | O | 1 | $C_{18}H_{37}$ |

The compounds of the present invention can be prepared by reacting known compounds of formula (V)

$$[NC-CH_2-CO-X\tfrac{}{}]_n A \qquad (V)$$

wherein X, A and n are as above defined, with a minimum n equivalents of trimethyl- or triethylorthoformate and minimum n equivalents of a compound of formula (VI)

(VI)

wherein R, $R_1$, $R_2$, and $R_3$ have the above mentioned meanings.

The reaction is carried out in a polar organic preferably an alcohol, such as for example n-solvent, propyl, n-butyl, isobutyl alcohol or ethylene glycol, diethylene glycol, propylene glycol, ethylene glycol monomethyl- or monoethyl ether.

Reaction temperature can range from 50° C. to 200° C., preferably between 100° and 150° C.

The obtained compounds are recovered and purified by means of well-known methods.

In another embodiment, the preparation of compounds (I), when n is 2, or when n is 1 and A is different from methyl or ethyl, can be carried out also by reacting a compound of formula (VII)

(VII)

wherein R, $R_1$, $R_2$, and $R_3$ have the above mentioned meanings and $R_{10}$ is methyl or ethyl, with compounds of formula (VIII)

$$A-(XH)_n \qquad (VIII)$$

wherein A, X and n have the above meaning.

In this case the reaction is preferably carried out in the presence of a transesterification catalyst, such as for example a tetraalkyl titanate or a sodium or potassium alcoholate in an apolar solvent, such as for example toluene, xylene or even in the absence of any solvent.

The compounds of the present invention are endowed with a very effective capacity of absorbing UV radiations; particularly UV component of sunlight, especially the radiation between 230 and 360 nm.

Therefore, the compounds of the present invention are useful as sunscreens and photostabilizers and a method for using them as sunscreens, particularly in cosmetics and as photostabilizers for organic materials, particularly polymers, is an object of the present invention.

According to a first embodiment of the present invention, the cosmetic compositions for the protection of skin from sun radiations, comprise at least a compound of formula (I) in admixture with conventional vehicles and excipients. The amounts of the compound of formula (I) will range from 0.1 to 20%, preferably from 0.5 to 15% by weight with respect to the total weight of the composition.

The cosmetic compositions of the present invention are useful for the protection of skin against sun radiation. A cosmetic treatment for the protection of skin against sun protection is comprised in the present invention.

The cosmetic compositions containing at least a compound of formula (I) according to the present invention, other than the skin treatment, are useful for the treatment of hair and make-up.

Said compositions may be of various kinds, such as for example, solutions, lotions, water-in-oil or oil-in-water emulsions, or in the form of gels, lipsticks, sprays.

Said compositions can be prepared by means of conventional techniques which are well-known to those skilled in the art, by formulating generally used ingredients, such as for example oils, fats, emulgents, hydrating agents, emollients, preservatives, surfactants, thickeners, antifoaming, perfumes, pigments, dyes, and many others, such as alcohols, polyols, electrolytes, silicone derivatives. The most used solvents are caprinic or caprilic acid triglycerides, for example castor oil, fatty acid esters with isopropanol, propylene glycol, glycerine, propylene glycol monomethyl or monoethyl or monobutyl ether.

In a particular embodiment, the cosmetic compositions according to the present invention may contain in combination also well-known sunscreens, particularly those whose maximum absorption is between 290 and 320 nm.

Well-known sunscreens, that may be combined with the compounds of formula (I) are for example:

3-(4-methylbenzylydene)camphor, 2-ethylhexyl-(4-dimethylamino)benzoate, 2-ethylhexyl-4-methoxycinnamate, mentyl salicilate, 2-hydroxy-4-methoxybenzophenone, 2,4,6-trianilino-(p-carbo-2-ethylhexyloxy)-1,3,5-triazine, tris(p-carboxyanilino)triazine derivatives disclosed in EP 0570838, salts of 2-phenylbenzimidazol-5-sulfonic acid or 2-hydroxy-4-methoxybenzophenone-sulfonic acid.

The cosmetic compositions according to the present invention, other than at least a compound of formula (I), may also contain inorganic pigments usually employed in cosmetics for the protection of skin against UV radiation, such as titanium or zinc or silicon or aluminium oxides.

The compounds of formula (I) above described can be used also to stabilize the compositions themselves against the UV radiation, comprising sun radiation. In this case, it relates to compositions whose ingredients can undergo undesired degradation or discolorations due to light, such as for example shampoos and hair lacquers, hair-styling lotions, compositions for hair dyeing, formulates for make-up, such as nail lacquers, foundation, lipstick.

Therefore, it is another object of the present invention a method for protecting a cosmetic composition from the degradation induced by UV radiation which comprises incorporating an effective amount of at least a compound of formula (I).

According to a second embodiment of the present invention, the compounds of formula (I) are used as photo-stabilizers for organic materials, in particular synthetic polymers and paints. As synthetic polymers it is meant polyethylene, polypropylene, polystyrene, polybutadiene, polyisoprene and copolymers thereof, polyvinyl acetate and copolymers thereof, particularly with polyethylene, polyesters, such as polyethyleneterephthalate, polyamides, such as Nylon 6 and Nylon 6.6, polyurethanes, polyacrylates, polymethacrylates, polyvinylchloride The compounds of formula (I) can be incorporated in the polymers to be stabilized by means of every method known in the art for admixing additives to polymeric materials; for example, they can be admixed with the polymer in a suitable mixer, or added in the form of a solution or a suspension in a suitable solvent, such as methanol, ethanol, acetone, chloroform, subsequently removing the solvent after the mixing with the polymer, which can be in the form of a powder, granulate or suspension, or they can be added to the polymer during its preparation, for example in the last step of preparation.

The compound of formula (I) can also be used in combination with other stabilizers and additives generally used for polymers, such as for example phenol-based antioxidants, phosphites, hindered amines, particularly those containing the 2,2,6,6-tetramethylpiperidine group in their structure, other UV-absorbers based on benzotriazoles or benzophenones, plasticizers, lubricants, antistatic agents, flame retardants, titanium oxide.

The amount of compounds of formula (I) necessary for an effective stabilization of the polymer depends on several factors, such as the polymer type and characteristics, its intended use, radiation intensity, exposition duration and the optional presence of other stabilizers. Generally an amount ranging from 0.01 to 5%, preferably from 0.05 to 2%, by weight of the polymer is sufficient.

Therefore, another object of the present invention is a method for protecting synthetic polymers and paints from photodegradation comprising the addition of at least a compound of formula (I).

The following examples illustrate the invention.

EXAMPLE 1

A mixture consisting of 23.7 g of ethylcyanoacetate, 42 g of 2-(p-aminophenyl)benzofuran, 34 g of triethyl formate in 150 ml of ethylene glycol was slowly heated up to 150° C., distilling the forming ethyl alcohol at the same time and stirring for 2 hours.

After cooling the mixture down to 70° C., 100 ml of methanol were added and temperature was brought down to 10° C.

The formed precipitate was filtered, washed with methanol, dried and crystallized from xylene obtaining the compound of the following formula with m.p. 195°–197° C. and $E'_1$ of 1611 at 352 nm.

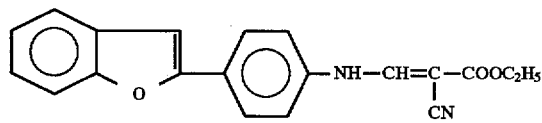

EXAMPLE 2

13.3 g of the compound of Example 1 were added to 78 g of 2-ethylhexyl alcohol. 0.2 mg of tetrabutyl orthotitanate were added and the mixture was heated to 150° C.

Therefore the mixture was stirred for 3 hours between 150° and 170° C., distilling the forming ethyl alcohol at the same time.

2-Ethylhexyl alcohol excess was vacuum-distilled and the residue was crystallized from n-octane.

The compound of the following formula with m.p. 122°–124° C. and $E'_1$ of 1339 at 353 nm was obtained.

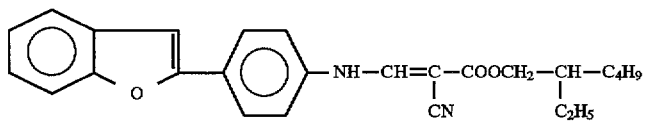

Operating as described in Example 1 or 2, the compounds listed in the following Table 2 were obtained:

TABLE 2

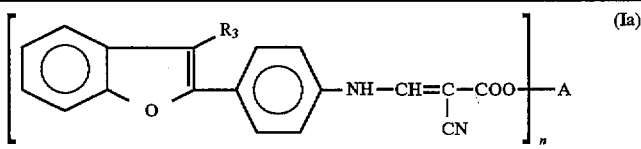

| EXAMPLE | R₃ | n | m.p. °C. | A | λnm | E₁¹ |
|---|---|---|---|---|---|---|
| 3 | CH₃ | 1 | 203–206 | —C₂H₅ | 350 | 1427 |
| 4 | H | 1 | 112–115 | —C₁₀H₂₁ | 353 | 1230 |
| 5 | H | 1 | 219–221 | (2,2,6,6-tetramethyl-1-methylpiperidinyl) | 354 | 1218 |
| 6 | H | 1 | 122–125 | —CH₂—CH₂—O—CH₂—CH₂OCH₃ | 353 | 1334 |
| 7 | H | 1 | 113–115 | —CH₂—CH₂—O—CH₂—CH₂—O—C₄H₉ | 353 | 1265 |
| 8 | H | 1 | 132–133 | —C₁₂H₂₅ | 355 | 1185 |
| 9 | CH₃ | 1 | 84–88 | —CH₂—CH(C₂H₅)—C₄H₉ | 351 | 1172 |
| 10 | CH₃ | 2 | 197–201 | —(CH₂)₁₀— | 356 | 1242 |
| 11 | H | 1 | 118–124 | —C₁₈H₃₇ | 355 | 999 |

EXAMPLE 12

Preparation of an alcoholic gel

| | |
|---|---|
| Propylene glycol | 25.0 g |
| Ethyl alcohol 96% | 25.0 g |
| Synthalen® M (crosslinked polyacrylic acid from 3V-Sigma) | 0.6 g |
| Compound of Example 8 | 2.0 g |
| Triethanolamine | 0.3 g |
| Preservative | 0.3 g |
| Perfume | 0.3 g |
| Distiled water q.s. to | 100 g |

Synthalen M is dispersed in water, then triethanolamine is added and subsequently the mixture of propylene glycol and ethanol wherein Compound of Example 8 was dissolved.

EXAMPLE 13

Preparation of a lipstick

| | |
|---|---|
| Beeswax | 13.0 g |
| Carnauba wax | 7.5 g |
| Lanolin | 5.0 g |
| Isopropyl myristate | 8.0 g |

-continued

Preparation of a lipstick

| | |
|---|---|
| Mineral oil | 3.0 g |
| Castor oil | 63.5 g |

85 g of this mixture are warmed to melt, 7 g of the compound of Example 1 and 8 g of 3-(4-methylbenzylydene)camphor, as well as perfume, aroma and dyes are added to the melt then it is diluted with castor oil to 1000 g and cooled to room temperature.

EXAMPLE 14

| Preparation of a sun creme | |
|---|---|
| C₁₂–C₁₅ alcohols benzoate (Finasol® TN, Witco) | 5.0 g |
| Cetylstearyl alcohol | 3.0 g |
| Glycerine mono and distearate | 4.0 g |
| Polyglycol (Arlacel® 165 ICI) | 2.0 g |
| Myristic alcohol with 3 moles of propylene oxide (Witconol® APM, Witco) | 21.0 g |
| Compound of Example 2 | 2.5 g |

-continued

| Preparation of a sun creme | |
|---|---|
| 2-Ethylhexyl-4-methoxy cinnamate | 3.5 g |
| Perfume | 0.3 g |
| Distiled water q.s. to | 100 g |

Fatty phase is warmed at 80°–90° C., the compound of Example 2 is added, then the mixture is added to water, containing the hydrosoluble compounds, warmed to 80°–90° C. The mixture is stirred till warm for 15–20 minutes. The mixture is slowly cooled down and perfume is added.

EXAMPLE 15

| Preparation of a sun milk | |
|---|---|
| Fatty acid triglyceride | 20.0 g |
| Cetyl alcohol | 2.0 g |
| Cetylstearyl alcohol | 2.0 g |
| Lanolin | 4.0 g |
| Silicon oil | 0.4 g |
| 2-Ethylhexyl-4-dimethylamino benzoate | 2.5 g |
| Compound of Example 11 | 2 g |
| Abiol ® (preservative of 3V-Sigma) | 0.2 g |
| Synthalen ® M (crosslinked polyacrylic acid from 3V-Sigma) | 0.1 g |
| Triethanolamine | 0.15 g |
| Perfume | 0.3 g |
| Distiled water q.s. to | 100 g |

The preparation is carried out according to the procedure of Example 14.

EXAMPLE 16

| Preparation of a day-cream | |
|---|---|
| $C_8$–$C_{12}$ acid triglyceride | 29.0 g |
| Glycerine mono stearate | 7.0 g |
| Stearic acid | 2.0 g |
| Lanolin | 4.0 g |
| Preservative | 0.2 g |
| Compound of Example 10 | 2.5 g |
| Propylene glycol | 2.5 g |
| Triethanolamine | 0.5 g |
| Perfume | 0.3 g |
| Distiled water q.s. to | 100 g |

The preparation is carried out according to the procedure of Example 14.

EXAMPLE 17

1,000 g of low density-polyethylene (Riblene ®) EF 2100 Enichem), 2 g of n-octadecyl-3-(3,5-ditert-butyl-4-hydroxyphenyl)propionate, 1 g of calcium stearate and 0.3 g of a compound of formula (I) were admixed homogeneously. The obtained mixtures were extruded at 190° C. and transformed into granules. From these, by pressing at 200° C., films having 0.2 mm thickness were obtained.

Samples of these films were subjected to UV radiations in a Weatherometer WOM Ci-65 at a temperature of the black panel of 63° C. In the irradiated samples the increase of the carbonyl band in the infrared region at 5.85 nm and the time necessary to have an increase of 0.1 of the carbonyl band were measured in comparison with a film not containing the stabilizer of formula The results are reported in the Table 3 below.

TABLE 3

| Stabilizer | T 0.1 (hours) |
|---|---|
| Without stabilizer | 360 |
| Compound of Example 2 | 1170 |
| Compound of Example 5 | 1350 |
| Compound of Example 10 | 1230 |

We claim:

1. A compound of the formula (I)

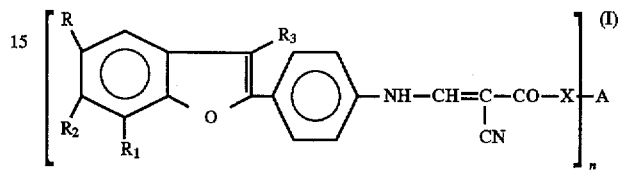

wherein

R and $R_1$, which can be the same or different, are hydrogen or a $C_1$–$C_8$ straight or branched alkyl group, $R_2$ is hydrogen or the group $OR_4$, wherein $R_4$ is a $C_1$–$C_4$ alkyl group, $R_3$ is hydrogen, methyl or ethyl, X is oxygen or the $NR_5$ group, wherein $R_5$ is hydrogen or $C_1$–$C_{18}$ straight or branched alkyl group n is the number 1 or 2, A, when n is 1, is a $C_1$–$C_{20}$ straight or branched alkyl group, $C_6$–$C_{12}$ cycloalkyl group, the group of formula (II),

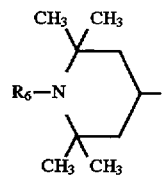

wherein $R_6$ is hydrogen or methyl group or a group of formula (III)

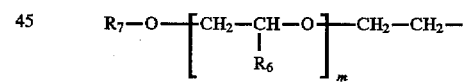

wherein $R_6$ has the above meanings and $R_7$ is $C_1$–$C_{18}$ straight or branched alkyl group, phenyl, phenyl substituted with a $C_1$–$C_4$ straight or branched alkyl group, m can have the values from 0 to 4, A, when n is 2, is $C_2$–$C_{12}$ alkylene or the group of formula (IV)

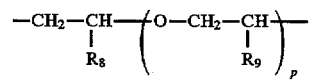

wherein $R_8$ and $R_9$, which may be the same or different, are hydrogen or methyl group, p is a number from 1 to 4.

2. A compound according to claim 1, wherein X is oxygen.

3. A compound according to claim 1, wherein X is oxygen, and $R_2$ is hydrogen.

4. A compound according to claim 1, selected from the group consisting of:

| | R | R₁ | R₂ | R₃ | X | n | A |
|---|---|---|---|---|---|---|---|
| 1 | H | H | H | H | 0 | 1 | C₂H₅ |
| 2 | H | H | H | H | 0 | 1 | CH₂CH—C₄H₉<br>\|<br>C₂H₅ |
| 3 | H | H | H | CH₃ | 0 | 1 | C₂H₅ |
| 4 | H | H | H | H | 0 | 1 | C₁₀H₂₁ |
| 5 | H | H | H | H | 0 | 1 |  CH₃—N⟨ring⟩ |
| 6 | H | H | H | H | 0 | 1 | (CH₂)₂O(CH₂)₂OCH₃ |
| 7 | H | H | H | H | 0 | 1 | (CH₂)₂O(CH₂)₂OC₄H₉ |
| 8 | H | H | H | H | 0 | 1 | C₁₂H₂₅ |
| 9 | H | H | H | CH₃ | 0 | 1 | CH₂—CH—C₄H₉<br>\|<br>C₂H₅ |
| 10 | H | H | H | CH₃ | 0 | 2 | (CH₂)₁₀ |
| 11 | H | H | H | H | 0 | 1 | C₁₈H₃₇ |

5. A process for the preparation of a compound of claim 1, by reacting a compound of formula (V)

$$[NC-CH_2-CO-X]_n-A \qquad (V)$$

wherein X, A and n are as above defined,
with a minimum n equivalents of trimethyl- or triethylorthoformate and minimum n equivalents of a compound of formula (VI)

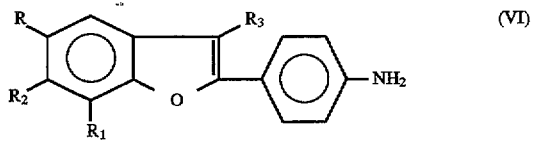

(VI)

wherein R, R₁, R₂, and R₃ have the above defined meanings.

6. A process for the preparation of a compound of claim 1, wherein n is 1 or 2 and A is different from methyl or ethyl, by reacting a compound of formula (VII)

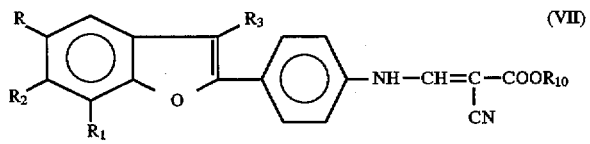

(VII)

wherein R, R₁ R₂ and R₃ are as above defined, R₁₀ is methyl or ethyl, with compounds of formula (VIII)

$$A-(XH)_n \qquad (VIII)$$

wherein A and X are as above defined and n is 1 or 2.

7. A method for protecting synthetic polymers and paints against photodegradation comprising the addition of at least a compound of claim 1 to the polymers and paints.

8. The method according to claim 7, comprising admixing with the polymers and paints at least a compound of formula (I).

9. The method according to claim 7, comprising the addition to the polymers and paints of a solution of a compound of formula (I) and subsequent evaporation of the solvent.

10. A method for the photostabilization of polymers, comprising an addition of a compound of formula (I) during a preparation of the polymer.

11. A cosmetic composition containing an amount ranging from 0.1 to 20% by weight with respect to the total amount of the composition of at least a compound of claim 1 in admixture with suitable cosmetic vehicles and excipients.

12. A composition according to claim 11, further containing a sunscreen.

13. A composition according to claim 12, wherein the sunscreen has a maximum absorption ranging from 290 and 320 nm.

14. A composition according to claim 13, wherein the sunscreen is selected from the group consisting of 3-(4-methylbenzylydene)camphor, 2-ethylhexyl-(4-dimethylamino)benzoate, 2-ethylhexyl-4-methoxycinnamate, mentyl salicilate, 2-hydroxy-4-methoxybenzophenone, 2,4,6-trianilino-(p-carbo-2-ethylhexyloxy)-1,3,5-triazine, tris(p-carboxyanilino)triazine derivatives, salts of 2-phenylbenzimidazol-5-sulfonic acid or 2-hydroxy-4-methoxybenzophenone5-sulfonic acid.

15. A composition according to claim 11, further containing one or more inorganic pigments suitable for cosmetic use.

16. A composition according to claim 11, in the form of a solution, lotion, emulsion, gel, lipstick, spray.

17. A method for protecting human skin against sunlight radiation, comprising the application to the skin of the cosmetic composition of claim 11.

18. A method for preparing a cosmetic composition with high sun protecting factor, comprising the addition to the composition of at least a compound of claim 1.

19. A method for protecting a cosmetic composition from UV radiation induced degradation comprising incorporating at least a compound of claim 1 in the composition.

20. The method according to claim 19, wherein the composition is a shampoo, hair lacquer, hair-styling lotion, hair dye, a cosmetic for make-up.

21. The method of claim 6, wherein the reaction is carried out in the presence of a transesterification catalyst.

* * * * *

UNITED STATES PATENT AND TRADEMARK OFFICE
CERTIFICATE OF CORRECTION

PATENT NO. : 5,665,334

DATED : September 9, 1997

INVENTOR(S) : Giuseppe RASPANTI and Giorgio ZANCHI

It is certified that error appears in the above-identified patent and that said Letters Patent is hereby corrected as shown below:

On the title page of the patent, at section "[54]", and at column 1, lines 1-4, please change the title to read as follows: --BENZOFURAN DERIVATIVES AND METHODS FOR THEIR USE AS STABILIZERS AND SUNSCREENS AGAINST UV RADIATIONS--.

Signed and Sealed this

Twenty-third Day of December, 1997

Attest:

BRUCE LEHMAN

Attesting Officer

Commissioner of Patents and Trademarks